US005748703A

United States Patent [19]

Cosman

[11] Patent Number: 5,748,703
[45] Date of Patent: May 5, 1998

[54] DYNAMIC COLLIMATOR FOR A LINEAR ACCELERATOR

[76] Inventor: Eric R. Cosman, 872 Concord Ave., Belmont, Mass. 02178

[21] Appl. No.: 685,199

[22] Filed: Jul. 23, 1996

Related U.S. Application Data

[63] Continuation of Ser. No. 216,584, Mar. 22, 1994, abandoned.

[51] Int. Cl.$^6$ ..................................................... G21C 1/02
[52] U.S. Cl. ........................... 378/152; 378/147; 378/148; 378/153
[58] Field of Search ............................ 378/145, 147, 378/148, 149, 150, 151, 152, 153, 156, 157, 158, 159, 160; 250/505.1

[56] References Cited

U.S. PATENT DOCUMENTS 5,237,599  8/1993  Gunji et al. ............................ 378/148

*Primary Examiner*—Don Wong
*Attorney, Agent, or Firm*—Richard J. Birch

[57] ABSTRACT

This invention relates to a novel dynamic collimator which can be adapted to a linear accelerator (LINAC). The collimator is such that the shape of the jaw arrangement, and therefore the collimated beam of X radiation from the LINAC, can be changed and conformed in a very flexible and versatile way. In a preferred embodiment of the invention, the collimator has three pairs of opposing, parallel jaws, each pair of jaws being moveable, under control, to open and close in variable amounts. Each set of pairs may be oriented at a 60° orientation such that the open transmission area of the collimator has a hexagonal shape. Variations on this sixth jaw collimator, including larger numbers of jaws, also are included within the invention. The variety of shapes with such a variable hexagonal collimator is enormous. Irregular target volumes can be filled by beams of radiation that can be nested because of the hexagonal nature of the jaw configuration, giving it added conformal shaping capabilities. Variable angles of orientation between the jaw pairs are also included within the invention so that rectangular shapes may also be achieved.

9 Claims, 4 Drawing Sheets

DYNAMIC COLLIMATOR FOR A LINEAR ACCELERATOR

This application is a continuation of application Ser. No. 08/216,584 filed on Mar. 22, 1994 now abandoned.

BACKGROUND TO THE INVENTION

The use of linear accelerators (LINACs) for external beam irradiation of patients, principally for the treatment of cancerous tumors, is a well developed field. LINACs have been used for this purpose since the 1940's, and are common in most major hospitals. The use of the linear accelerator for stereotactic external beam irradiation, so-called stereotactic radiosurgery or stereotactic radiotherapy, has been developed since around 1984. One of the first papers by Winston and Lutz describes the general technique. Further papers by Kooy et al. and Nedzi et al. describe the general technique.

FIG. 1 shows a diagram of the LINAC in a general configuration for stereotactic or radiation therapy application. The patient's body 2 is on the LINAC couch 3, and a target 1 is identified within the patient's body and placed at the intersection of the LINAC axes, the axis 5 being the vertical axis about which the couch 3 rotates and axis 6 being the horizontal axis about which the gantry of the LINAC 11 rotates. A beam of radiation emanates from the LINAC towards the target position 1. The target position 1 is at the isocenter of the two axes 5 and 6 such that the radiation always passes through the point 1 at the isocenter. A collimator system 7 is attached to the face plate of the linear accelerator gantry 11 to collimate the beam into a pencil of radiation, either circular or of a shaped form. Also in the gantry of the LINAC are jaws 8A, 8B, 8C, and 8D, which are typically independent and moveable so as to create a field size with variable shape, typically of rectangular form. This can be used when the external collimator 7 is not in place for larger fields, typically in the thorax, pelvis, etc. The couch rotates on a bearing 4 within the floor, and the couch can move up and down on stand 20 so as to position the target 1 at LINAC isocenter.

Today's linear accelerators have the four jaw rectangular structures shown as 8A, 8B, 8C, and 8D, and for the stereotactic application, an external collimator 7 is bolted on with typically circular or, in some cases, shaped cut static blocks to reduce the beam size according to the treatment to be done. These external collimators can be referred to as static field blocks. The jaws 8A through 8D can be considered to be moveable or dynamic collimation or jaws.

FIG. 2 illustrates further prior art and diagramatically shows the kinds of collimators that have been implemented on linear accelerators prior to the present invention. FIG. 2A illustrates the four moveable rectangular jaws 201A, 201B, 202A, and 202B. These move in Cartesian axes, and each jaw moves independently so that the rectangular shape 232 can take on various sizes and proportions, but always in rectangular form. It is also indicated that the orthogonal axes 231 and 232, along which the respective jaws, can be moved in orientation as indicated by the arrow vector. This would correspond to a rotation of the entire head of the gantry, which is possible on most linear accelerators. Thus, the rectangular field shape can be oriented in angle relative to a central axis of gantry head rotation.

FIG. 2B shows a standard fixed circular aperture which is common to be placed in collimator housings such as housing 7 in FIG. 1. This would give a circular pencil of radiation onto the target volume. Typically, such circular collimators come in different inner diameter sizes so that one can achieve different fields. However, these different fixed circular sizes would have to be loaded by hand for each irradiation episode, which is laborious and gives only limited shape capabilities.

FIG. 2C illustrates the concept of a dynamic collimator similar to that proposed and built by Leavitt et al. This has four rotating jaws 205, 206, 207, and 208, each rotating around a pivot point axis as indicated by the arrows in the figure. The resultant shape 240, therefore, can take on non-rectangular aspects and has a considerable variability. This is an example of a "dynamic collimator" whose shape can be changed for each of the couch and gantry positions of the LINAC, and indeed can be changed as a function of time during the movements of the couch and gantry of the LINAC so as to create a dynamic beam irradiation process. The dynamic collimator of FIG. 2C has the disadvantage that the shapes are limited in number and do not nest geometrically so that they can be compounded to cover a larger irregular field with convolutions and complex variations.

FIG. 2D illustrates another type of conformal shaped collimator or dynamic collimator referred to as a multi-leaf collimator. These are now in clinical practice, and, for example, Varian, Inc., which makes linear accelerators, produces such a multi-leaf collimator for clinical trials. It consists of a series of multiple leaves, illustrated by the set 209A and 209B, which move in an opposing fashion. Typically these leaves have independent movement so that the gap between them can be varied and be asymmetric from the center. The series of leaves shown in FIG. 2D can therefore achieve an open space aperture indicated by the perimeter 250. It has a staircased character, but can assume a wide variety of shapes. The multi-leaf collimator of FIG. 2D has the disadvantage that it requires many moveable leaves to achieve a shape of interest, and thus the failure rate of all the motors and encoders associated with each leaf is problematic, and the system becomes complicated.

Thus, there is need for a dynamic collimator which can achieve a wide variety of shapes, but at the same time has a reduced number of moving parts for increased reliability and can be used to geometrically nest exposure areas so that by compound beam exposures very wide variations in shape and complexity of irradiation shape can be achieved.

Further, there is need for a dynamic collimator or field shape collimator which can achieve shapes that approximate rectangles, triangles, parallelepipeds, circles, and other geometric shapes with enough variation to encompass tumor projection shapes that are encountered clinically. The present shaped or dynamic collimators of the prior art do not satisfy these requirements.

It is therefore an objective of the present invention to overcome the aforestated difficulties and shortcomings of the prior art.

3

Figure 3B:
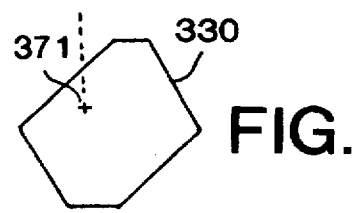
Figure 3C:
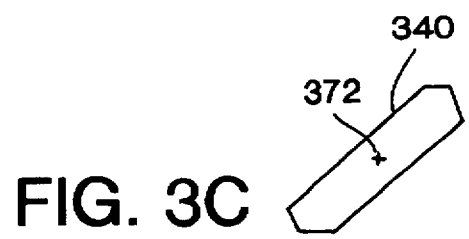
Figure 3A:
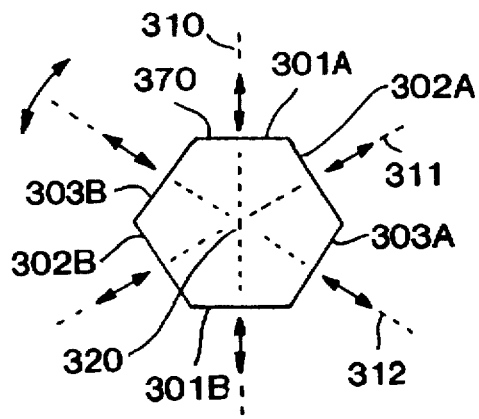
Figure 4A:
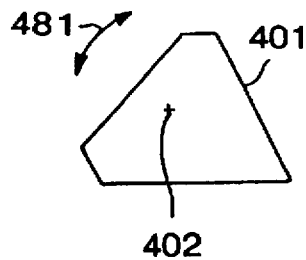
Figure 4B:
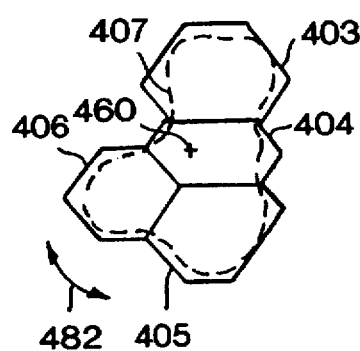
Figure 4C:
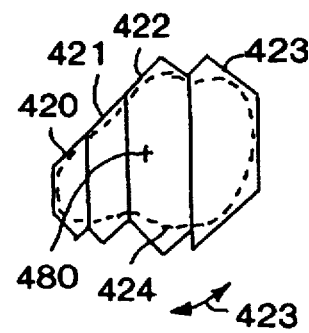

FIG. 3A shows a collimator shape with fixed jaws oriented 60% apart from each other;

FIG. 3B shows a collimator shape with unequal side lengths;

FIG. 3C shows another collimator shape with unequal side lengths;

FIG. 4A shows a collimator shape with adjacent jaw sides 60% apart;

FIG. 4B shows a collimator shape with multiple apertures to cover an irregular projection area;

FIG. 4C shows another collimator shape with multiple apertures.

Figure 5:
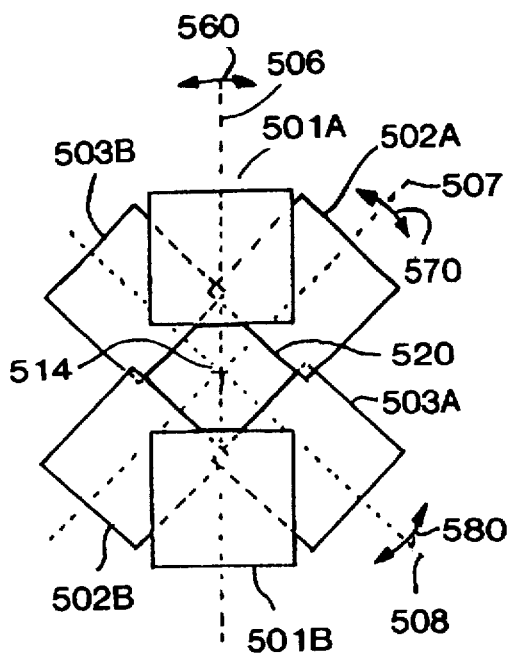

FIG. 5 shows a symmetric hexagonal jaw configuration for six independently moveable jaws to give hexagonal shaped field openings using the present invention.

Figure 6:
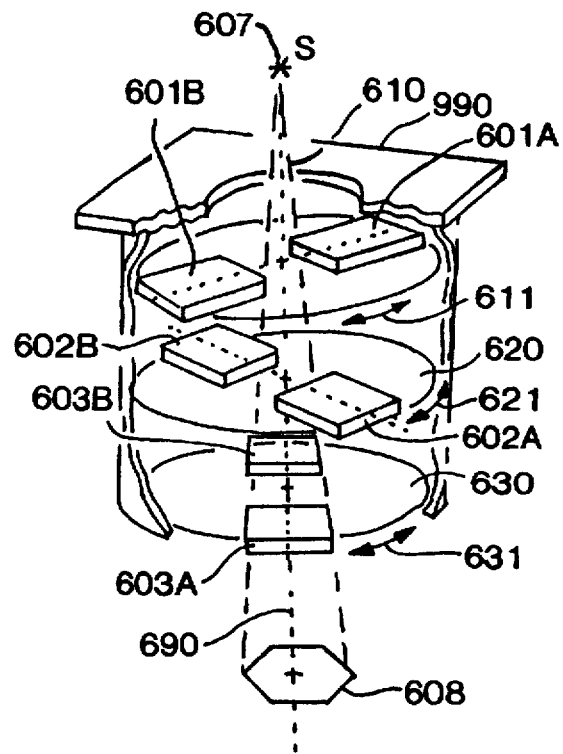

FIG. 6 shows a view of the stack of three tiers of jaws, each tier having two independent moveable jaws and the orientation of the jaws between tiers being registered by a phase angle.

Figure 7:
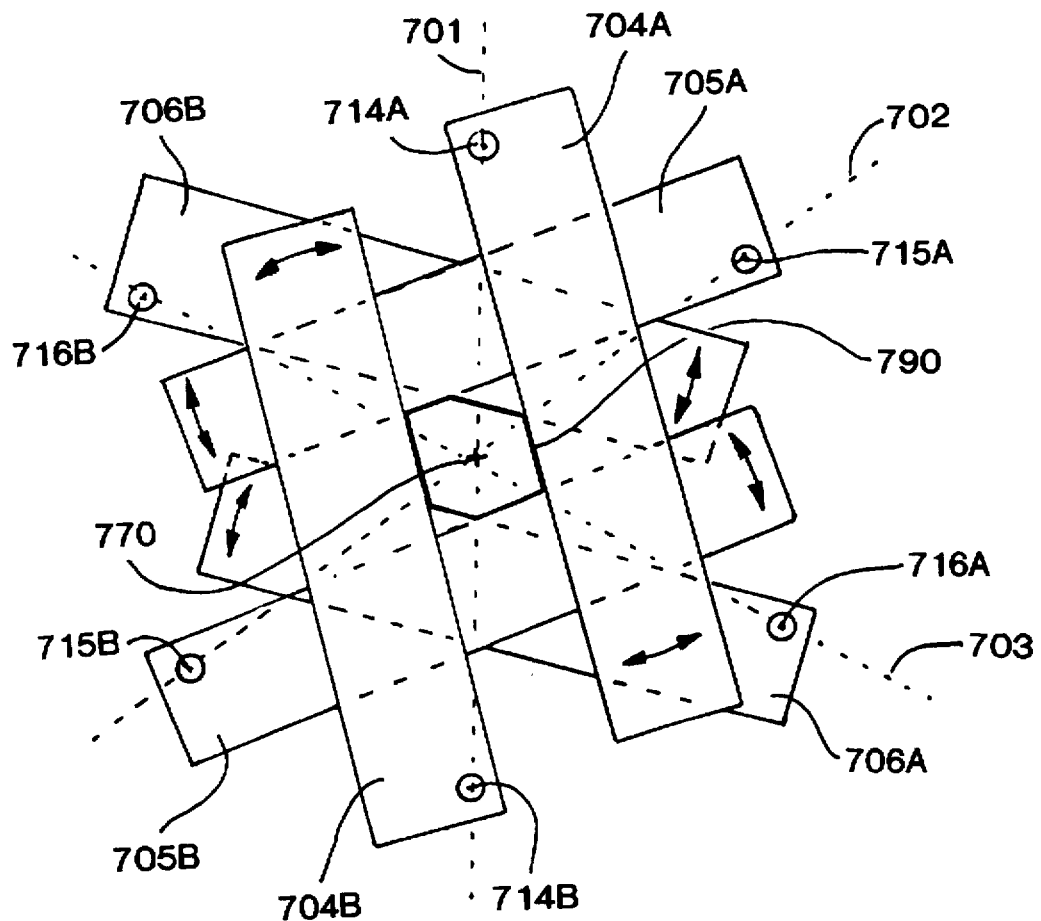

FIG. 7 shows a six jaw design with each jaw pivoting about an axis.

DESCRIPTION OF THE INVENTION

Referring to FIG. 3, in FIG. 3A is shown the samples of the collimator shapes that are possible with the present invention. In FIG. 3A, there are fixed jaws which are oriented 60° apart from each other, and each jaw being able to move independently inward toward a central point 320. In the embodiment of FIG. 3A, one sees the axes 310, 311, 312 which are oriented 60° apart from each other. The jaws 301A and 301B move parallel to the axis 310. The jaws 302A and 302B move parallel to the axis 311, and the jaws 303A and 303B move parallel to the axis 312. Thus, the figure that is the opening of the jaws, illustrated by the perimeter 370, is of hexagonal shape. It is not necessarily a regular isolateral hexagon, but it can be a highly irregularly shaped hexagon. Such variety of shapes is shown in FIGS. 3B and 3C. Because each of the six jaws moves independently of each other, the sides of the figures can take on larger or smaller lengths, and the deviation from the central point of convergence of the axes, illustrated by point 371 in FIG. 3B and 372 in FIG. 3C, need not be near the center of gravity of the resulting perimeter shapes 330 and 340 in the respective figures. Indeed, the central point need not be inside the opening of the apertures at all. In these figures, the opening represented by the various shapes corresponds to the portion of the collimator which the beam does not intercept; that is to say, it is the opening of the collimator.

The jaws of the collimator, which are not shown explicitly in FIG. 3, may be made out of high atomic number material of high density such as cerabend, tungsten, lead, etc. Thus, when the photon beam or X-ray beam from the accelerator strikes these jaws, it will attenuate the beam to a satisfactory extent that it can be considered "stopped." Thus, only the opening area will allow transmission of the X-rays in the shape of the collimator opening itself. This is modulated by magnification factors related to the X-ray source to target distance, but these are simple geometric considerations.

Figure 1:
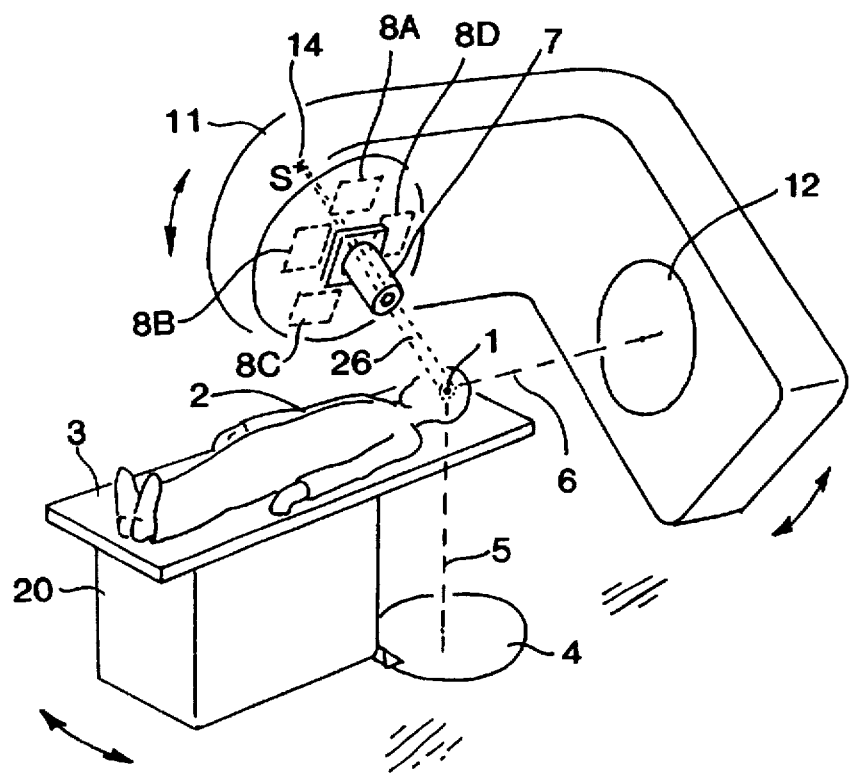
FIG. 1 shows the prior art, which is the general configuration of a linear accelerator (LINAC) irradiating a patient with a beam collimation system.
Figure 2A:
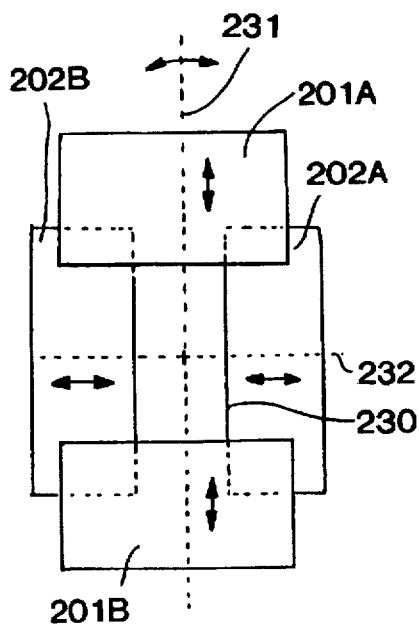
FIG. 2A shows a prior art collimator having four movable rectangular jaws.
Figure 2D:
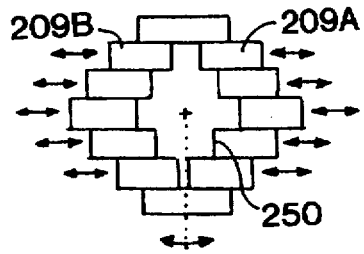
FIG. 2D shows a prior art multi-leaf collimator.
Figure 2B:
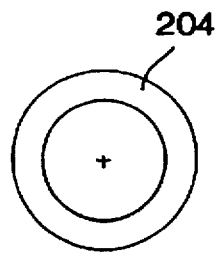
FIG. 2B shows a prior art collimator having a fixed, circular aperture.
Figure 2C:
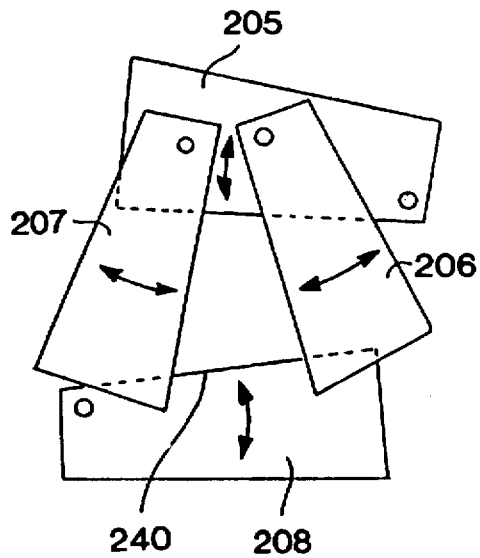
FIG. 2C shows a prior art dynamic collimator having rotating jaws.

Of interest in FIG. 3, relative to the present invention, is that in FIG. 3A the regular isolateral hexagon approximates the shape of a circular field such as that in FIG. 2A. The shape 330 in FIG. 3B approximates the shape of a parallelogram or a rectangle, if one wishes. The FIG. 340 in FIG. 3C approximates the shape of a thin, long rectangle. This variety of shapes is important in encompassing a tumor projection from any angular direction of the LINAC toward a target volume within the patient. In this example, the field shapes from such opposing jaw configurations are able to be convex hexagons, although if some jaws are pulled back, these will reduce to five, four, or three-sided convex polygons.

FIG. 4 further illustrates the flexibility in producing shaped collimation apertures with the hexagonal jaw arrangement. In FIG. 4A, the axis convergence point 402 is within the perimeter shape 401 represented by the jaw openings. 401 is nearly triangular in shape with chamfered corners. In FIG. 4B is shown the use of multiple apertures to cover a highly irregularly shaped tumor projection by area filling. The dashed line 407 may represent the irregular shape of a tumor as viewed from a given beam direction. To adequately expose this tumor to radiation, one would need a shape of collimator which approximates the profile of the tumor itself. This can be done straightforwardly with the dynamic shape conformal collimator of the present invention. The collimator, because of its hexagonal jaw arrangement, enables nesting or clustering of independent smaller shapes, illustrated by the Jaws 403, 404, 405, and 406. Each of these individual shapes are hexagons, and their sides abut exactly to produce the overall perimeter shape which essentially approximates the shape of the dashed tumor contour 407 yet avoids overlaps or missed areas to give excellent area filling. Note that the central axis 460 may represent the central direction of the overall collimator housing which holds the moveable jaws. Since the jaws can traverse past the central position independently, one can, with a single gantry and couch setting, move the jaws so that the independent shapes 403 through 406 can be located lateral to and displaced from the principal axis position 460 so as to contour to the tumor.

It is noted that if the axes 310, 311, and 312 in FIG. 3A are oriented 60 degrees apart, then the jaws will form a field shape 370 which is a convex hexagon with an included angle of 120 degrees between adjacent sides. If you pull one jaw back far enough to be non-intercepting of the beams, adjacent sides could be 60 degrees apart as in FIG. 4A. If the axes 310, 311, and 312 are made to vary in angle, then the hexagon of 5, 4, or 3 sided degenerate field shapes can have different included angles between adjacent sides. This is all included in the present invention.

FIG. 4C illustrates another utilitarian application for the present dynamic collimator. A tumor with irregular shape 424 is illustrated by the dashed line. To encompass this shape, one can divide the tumor into a series of thin, hexagonal, prismatic sections. These are approximated by the present invention's capabilities in the form of the shapes 420, 421, 422, and 423. Each shape is achieved by independent settings of the six jaws. Again, the central axis 480 represents the nominal axis of the overall collimator, and the jaws then move independent of that to achieve the various prismatic shapes. It is worth noting that in each of these figures the entire figure can be rotated as a rigid body, illustrated by the arrows 481, 482, and 483, around the axis point 402, 460, and 480, respectively. Thus, the entire geometry has a rotational degree of freedom which is easily achieved by the rotation of the face plate of the linear accelerator or an independent rotation axis for the collimator itself.

Referring to FIG. 5, one sees a view along the beam or radiation direction looking at the jaws of a hexagonal, dynamically shaped collimator system of the present invention. Point 514 may be the principal axis or a rotation axis of the system. This might be thought of as the central ray of the cone of radiation. The jaws 501A and 501B move along the axis 506, represented by the dashed line. Axis 506 is essentially perpendicular to the radiation direction indicated by the point 504, which is the axis of rotation, for example, of the entire collimator housing. Similarly, jaw 502A and jaw 502B move along the direction 507. Jaws 503A and 503B move along the axis 508. Each pair of jaws may be attached mechanically in a mechanical level or a tier so that there is a stack of three tiers, each tier containing a pair of independently moving jaws as shown in FIG. 5. As the jaws move in and out and assume a particular position relative to the central axis 514, they then achieve an aperture shape indicated by the shape 520, which is six-sided, or hexagonal. The construction of this assembly might be such that each tier of jaws may rotate around the axis 514 independently, or they may rotate in unison. The indication of rotation is indicated by the arrows 560, 570, and 580 for the three different tiers of independent jaw pairs. The axes 560, 570, and 580 are oriented 60° apart from each other; then, for square or straight jaws, as shown in FIG. 5, the hexagon sides always appear at 60° to their adjacent side. If the tiers of jaws all rotate together, then the hexagonal shapes of collimator openings that result may be rotated in unison so that any given shape can assume any angular orientation around the axis 514. The uniform 60° hexagons with the jaws ganged at 60° to each other, rotating rigidly in unison, has an advantage of easily nesting the sides as shown, for example, in the illustrations of FIG. 4.

FIG. 6 illustrates an isometric view of how such a three-tiered dynamic collimator might be configured. The source S, represented by point 607, might be the source of X-ray radiation or electron beam radiation from a radiation delivery system such as a linear accelerator. The dashed lines 610 represent a beam of radiation which is aimed at a target volume within a patient's body. This target volume might be a cancerous tumor which must be irradiated for therapeutic reasons. The axis 690 might represent the rotation axis of the collimator housing represented by the structure 990 that has been sectioned so as to reveal in this diagram the inner assembly of tiers of jaws. The upper tier 640 has the moveable jaws 601A and 601B, which, when moving back and forth along their respective axis, intercept the cone of radiation 610 and thus clip the cone of radiation to achieve a final shape on the target, represented by beam projection spot 608. Similarly, in the second tier, represented by the plane of apparatus 620, the jaws 602A and 602B will move together on their respective axes, which is orthogonal to the rotation axis 690, so as to clip the beam in their phase angle of orientation. Similarly, the third tier, represented by the plane of apparatus 630, has jaws 603A and 603B, which similarly intercept the beam of radiation to produce the projection edge in their angle around the central axis relative to the central axis 690. The sum effect of these jaws moving will then produce the six-sided or hexagonal shape of the beam projection 608 that causes radiation to pass only through that perimeter onto the target volume within the patient's body.

The construction details of such a collimator, and in particular how the tiers of jaws and jaws move and are supported relative to the overall housing 690, is simple to imagine by a mechanical engineer. The tiers could be basically a mechanical frame which supports linear travels that hold the jaws and enable the jaws to move on their respective axes. The jaws may be made from a very heavy material such as lead, cerabend, or tungsten so as to attenuate the radiation when the radiation hits the jaws. The jaws may be moved quantitatively and their position known very accurately by any number of stepper motor, encoder, or linear readout means so that the exact position of the jaws, and therefore the configuration of the projection 608, is known electronically to control means which control the movements of the jaws according to the appropriate treatment plan.

There are many variations of the present invention which are possible by those skilled in the art. Addition of more jaws than six would increase the fine tuning of the shapes which are possible. Use of single jaws in each tier of the three tiers would also give a degree of variation that could be quite helpful in many treatment plans. The jaws, as illustrated in FIGS. 5 and 6, move on axes in an opposed, parallel fashion. There are other schemes in which the jaws of a six-jaw dynamic collimator could be actuated to give a rich zoology of shapes. There are jaw geometries and mechanisms which do not require the 3-tier arrangement to give hexagonal field shapes.

FIG. 7 illustrates such a variation of the present invention. In this situation, there is a central axis which is the symmetry axis, for example, of the housing. There are three axes 701, 702, and 703 with associated jaws 704A and 704B, 705A and 705B, and 706A and 706B, respectively, which can pivot on the pivot points 714A and 714B, 715A and 715B, and 716A and 716B. This rotation is indicated by the arrows on each jaw. The resultant figure is illustrated by the hexagonal shape 790. Thus, FIG. 7 shows another way of achieving moveable, fixed jaws to achieve a hexagonal or quasi-hexagonal shape which relies on more of an iris type principle or rotatable jaws. There are ways of ganging the jaws together without using encoders such as geared movements on a ring gear or actuator to move the jaws in neither a translational nor a rotational movement, but rather at any angle or displacement relative to the central axis that one wishes. All such variations are possible to those skilled in the art. Furthermore, the jaws could have a curved shape so that at a given degree of opening they approximate more a circle for each angle or rotation or displacement. This is also claimed within the scope of the present invention. As has been alluded to previously, the axes associated with the pairs of jaws could rotate about this central axis independently so that the angle or phase angle of the axes, one relative to the other, could be varied. Thus, for example, in FIG. 5, rather than the jaws moving on a hexagonal arrangement, the axes could be oriented at 90° to each other and the shapes would then become square, rectangles, and so forth. Shapes other than regular hexagons could easily be achieved.

The jaws of the dynamic collimator can be controlled automatically by the treatment planning computer integrated with the record-and-verify or direct readout of the parameters of the linear accelerator. The jaws could be used in a quasi-static mode; that is to say, they can be moved and fixed in a given position and then the exposure made at a given gantry or couch angle of the LINAC, or they can be used in a fully dynamic mode where they are actually in motion as the gantry and couch angle of the LINAC are also in motion. A dynamic collimator as shown here can be used in conjunction with the standard square jaws of the LINAC itself, which are usually permanently installed within the gantry to increase the number of shapes that are possible. The dynamic collimator, as described in this invention, can be installed as an accessory to the linear accelerator, taken on and off during, before, and after a specific procedure which involves the stereotactic treatment.

Having described the invention herewith, what I claim by U.S. Letters Patent are the following:

1. A field-shaping collimator to be cooperatively connected to a radiation source which delivers radiation on a target volume inside a patient including:

a. a rotatable housing to attach to said radiation source and support said field-shaping collimator, said housing having essentially an axis which approximates the direction of the radiation beams from said radiation source, said radiation beams being oriented to aim at said target volume when said patient is to be radiated by said radiation source;

b. a first jaw tier, cooperatively connected to said housing and positioned at a first level along said axis, said first jaw tier including at least one first jaw tier moveable, straight edge jaw, which moves essentially perpendicular to said axis so as to intercept said radiation beam according to the position of said first jaw tier;

c. a second jaw tier, cooperatively connected to said housing and positioned at a second level along said axis, said second jaw tier including at least one second jaw tier moveable, straight edge jaw which moves essentially perpendicular to said axis so as to intersect said radiation beam according to the position of said second jaw tier moveable jaw; and, d. a third jaw tier cooperatively connected to said housing and positioned at a third level along said axis, said third jaw tier including at least one third jaw tier moveable, straight edge jaw tier which moves essentially perpendicular to said axis so as to intersect said radiation beams according to the position of said third jaw tier moveable jaw;

such that, when in use, the field shape of said radiation beams at said target volume is varied according to said first, second, and third jaw tier moveable, straight edge jaw position so as to improve the quality of said irradiation to said target volume.

2. The apparatus of claim 1 wherein each of said first, second, and third jaw tiers include two opposing, moveable straight edge jaws, each of which can move perpendicular to said axis and thereby intersect said radiation beams from essentially opposite sides of said radiation beams.

3. The apparatus of claim 2 in which at least one of said first, second and third jaw tiers can be rotated with respect to the other said jaw tiers such that the angular orientation of said straight edge jaws in said jaw tiers can be varied from one tier to another, thereby varying the angular orientation of one side of said field shape to an adjacent side of said field shape.

4. The apparatus of claim 1 in which said first, second and third jaw tiers are adapted to rotate about said axis so as to achieve different angular orientations of said field shapes at said target volume.

5. A field-shaping collimator to be cooperatively connected to a radiation source, such as a linear accelerator, which delivers radiation on a target volume inside a patient, including:

a. a housing to attach to said X-ray radiation source and support said field-shaping collimator, said housing having essentially an axis which approximates the direction of the radiation beams from said radiation source, said radiation beam being oriented to aim at said target volume when said patient is to be radiated by said radiation source;

b. a first jaw tier, cooperatively connected to said housing, positioned at a first level along said axis, said first jaw tier including two opposing, moveable jaws, each of which can move perpendicular to said axis and thereby intersect said radiation beams from essentially opposite sides of said radiation beams;

c. a second jaw tier, cooperatively connected to said housing, positioned at a second level along said axis, said second jaw tier including two opposing, moveable jaws, each of which can move perpendicular to said axis and thereby intersect said radiation beams from essentially opposite sides of said radiation beams;

d. a third jaw tier cooperatively connected to said housing positioned at a third level along said axis, said third jaw tier including two opposing, moveable jaws, each of which can move perpendicular to said axis and thereby intersect said radiation beams from essentially opposite sides of said radiation beams;

e. such that, when in use, the field shape of said radiation beams at said target volumes can be varied according to said first, second and third jaw tier moveable jaw configurations in which at least one of said first, second, and third jaw tiers can be rotated with respect to the other said jaw tiers such that the angular orientation of said jaws in said jaw tiers can be varied from one tier to another, thereby varying the angular orientation of one side of said field shape to an adjacent side of said field shape.

6. The apparatus of claim 5 in which said two opposing moveable straight edge jaws in said first, second, and third jaw tiers are oriented at 60 degree angular orientations from one tier to the adjacent tier so that said field shape of said radiation beams, as projected through said field shaping collimator form hexagonal shaped fields, each side of which hexagonal shaped field is at essentially a 120 degree included angle with respect to the adjacent side of said hexagonal shaped field.

7. The apparatus of claim 5 in which adjacent straight edge jaws are adapted to move in directions oriented 60 degrees to each other and essentially perpendicular to said radiation beams so that said field shape is able to be made a convex hexagon, the adjacent sides of said hexagon having a 120 degree included angle between them.

8. A field-shaping collimator to be cooperatively connected to a radiation source, such as a linear accelerator, which delivers radiation on a target volume inside a patient, including:

a. a housing to attach to said X-ray radiation source and support said field-shaping collimator, said housing having essentially an axis which approximates the direction of the radiation beams from said radiation source, said radiation beam being oriented to aim at said target volume when said patient is to be radiated by said radiation source and with said housing adapted to rotate about said axis so as to achieve different angular orientations of said field shapes at said target volume;

b. a first jaw tier, cooperatively connected to said housing, positioned at a first level along said axis, said first jaw tier including at least one first jaw tier moveable jaw, which moves essentially perpendicular to said axis so as to intercept said radiation beam according to the configuration and position of said first jaw tier;

c. a second jaw tier, cooperatively connected to said housing, positioned at a second level along said axis, said second jaw tier including at least one second jaw tier moveable jaw which moves essentially perpendicular to said axis so as to intersect said radiation beam according to the position and configuration of said second jaw tier moveable jaw;

d. a third jaw tier cooperatively connected to said housing positioned at a third level along said axis, said third jaw tier including at least one third jaw tier moveable jaw which moves essentially perpendicular to said axis so as to intersect said radiation beams according to the configuration of said third jaw tier moveable jaw;

e. such that, when in use, the field shape of said radiation beams at said target volumes can be varied according to said first, second and third jaw tier moveable jaw configurations, so as to improve the quality of said irradiation to said target volume.

9. A dynamic collimator for cooperative connection to a radiation source to create various field shapes of the radiation beams from said radiation source onto a target volume inside a patient including:

at least six moveable straight edge jaws being enclosed in a rotatable housing cooperatively connected to said radiation source which are adapted to intercept said radiation beams and to move in directions which are essentially perpendicular to said radiation beams, so as to be able to create a six-sided opening for said radiation beams, and thus a six-sided field shape of radiation beams onto said target volume.

* * * * *